United States Patent [19]

Prohaska

[11] Patent Number: 5,089,697
[45] Date of Patent: Feb. 18, 1992

[54] FIBER OPTIC SENSING DEVICE INCLUDING PRESSURE DETECTION AND HUMAN IMPLANTABLE CONSTRUCTION

[76] Inventor: Otto J. Prohaska, 2065 Hanover Dr., Cleveland Heights, Ohio 44112

[21] Appl. No.: 296,060

[22] Filed: Jan. 11, 1989

[51] Int. Cl.$^5$ .............................................. H01V 5/16
[52] U.S. Cl. ............................. 250/227.21; 250/227.14
[58] Field of Search ............... 250/227, 231 R, 231 P, 250/227.21, 231.1, 221, 227.15, 227.16, 227.14; 350/96.21, 96.15, 96.20; 73/705

[56] References Cited

U.S. PATENT DOCUMENTS

| 4,071,753 | 1/1978 | Fulenwider et al. | 250/227.21 |
| 4,293,188 | 10/1981 | McMahon | 250/237 G |
| 4,542,291 | 9/1985 | Zimmerman | 250/231.1 |
| 4,678,905 | 7/1987 | Phillips | 250/227.21 |
| 4,701,751 | 10/1987 | Sackett | 250/227.21 |
| 4,741,590 | 5/1988 | Caron | 350/96.21 |
| 4,803,353 | 2/1989 | Moorehead | 250/227 |

Primary Examiner—David C. Nelms
Attorney, Agent, or Firm—Calfee Halter & Griswold

[57] ABSTRACT

A fiber optic sensing device for use in a variety of different applications is disclosed. The fiber optic sensing device includes a light source and a first fiber optic waveguide for receiving light from the light source. A second fiber optic waveguide is provided for receiving light from the first fiber optic waveguide. The fiber optic sensing device further includes means mounting the first and second fiber optic waveguides for relative movement to vary the light transmitted between the first and second fiber optic waveguides. A sensor is provided for sensing the light transmitted between the first and second fiber optic waveguides.

22 Claims, 4 Drawing Sheets

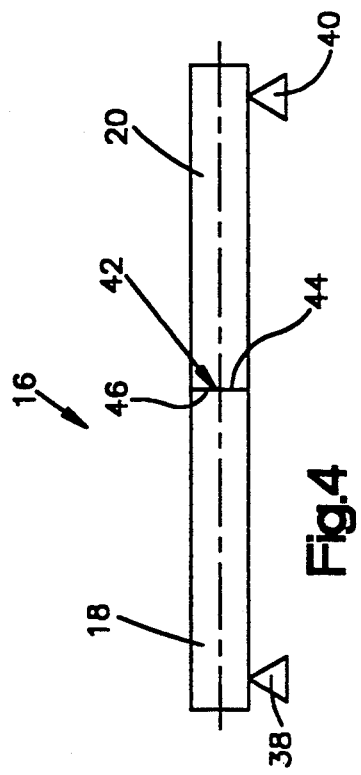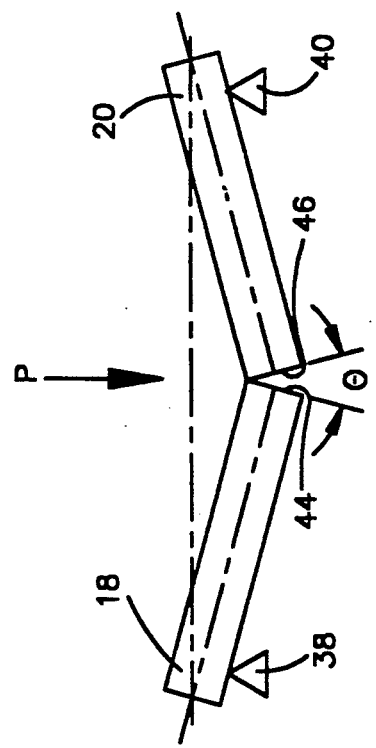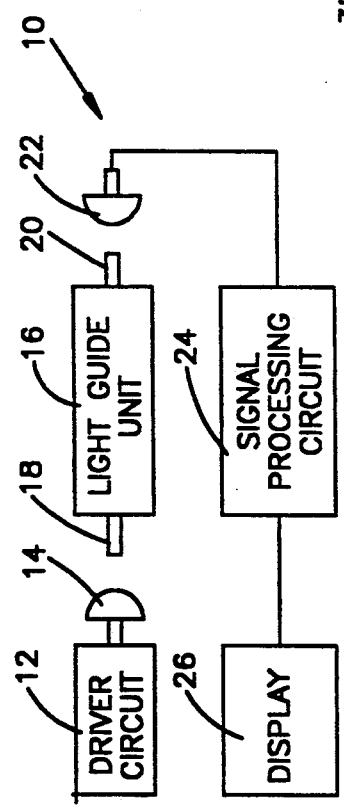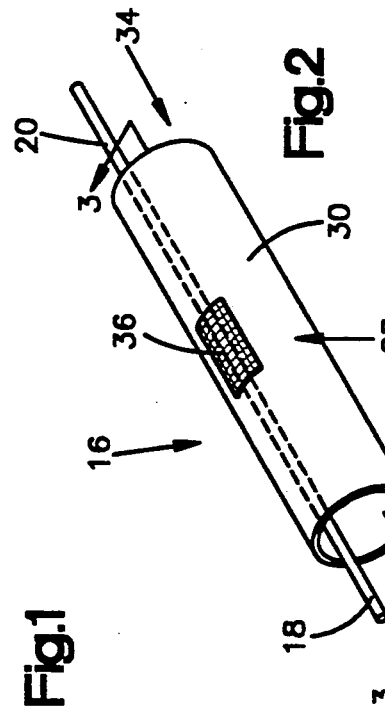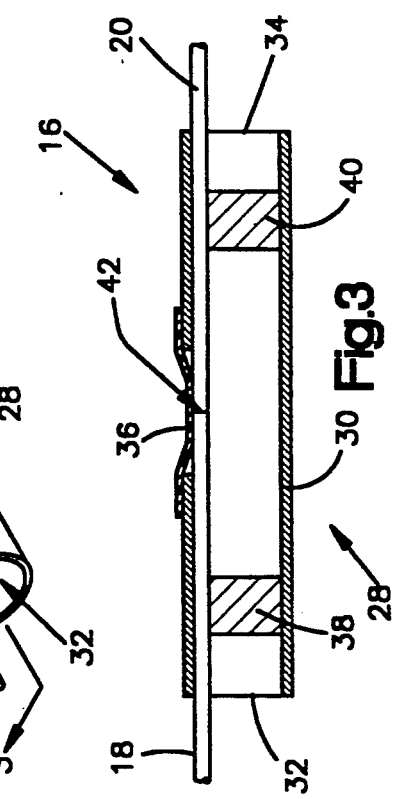

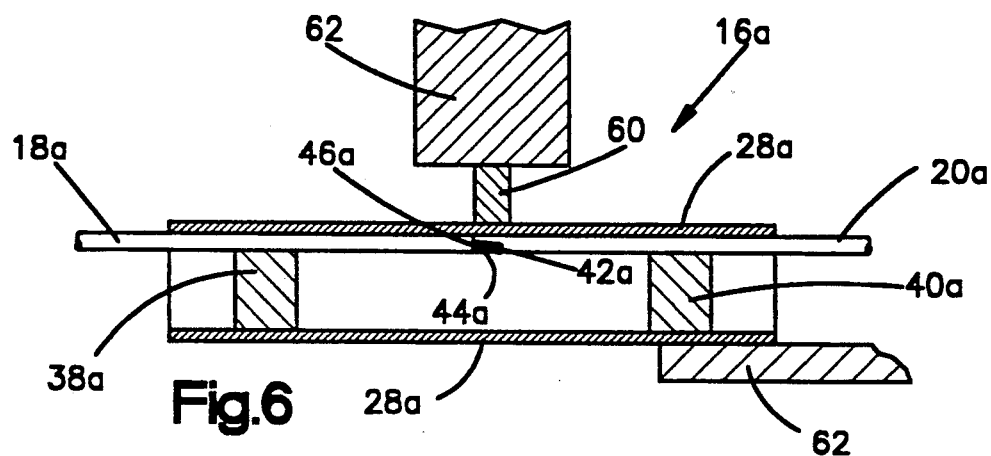
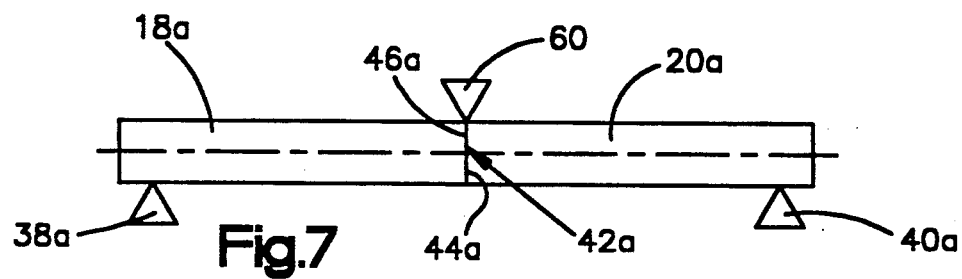
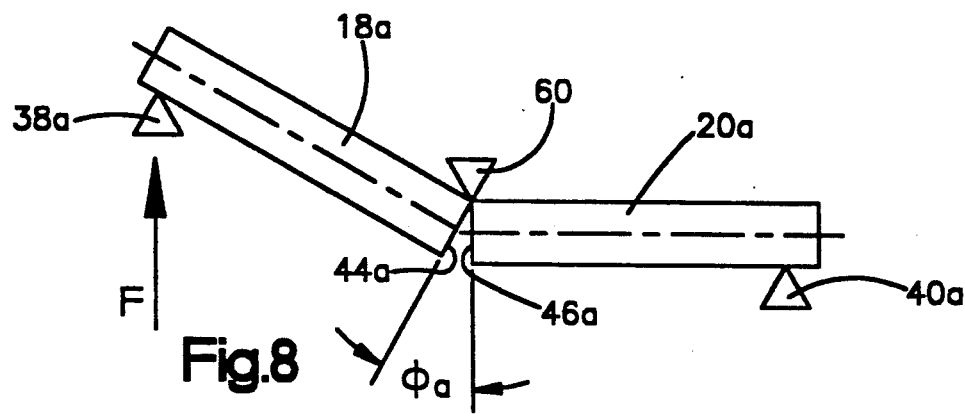

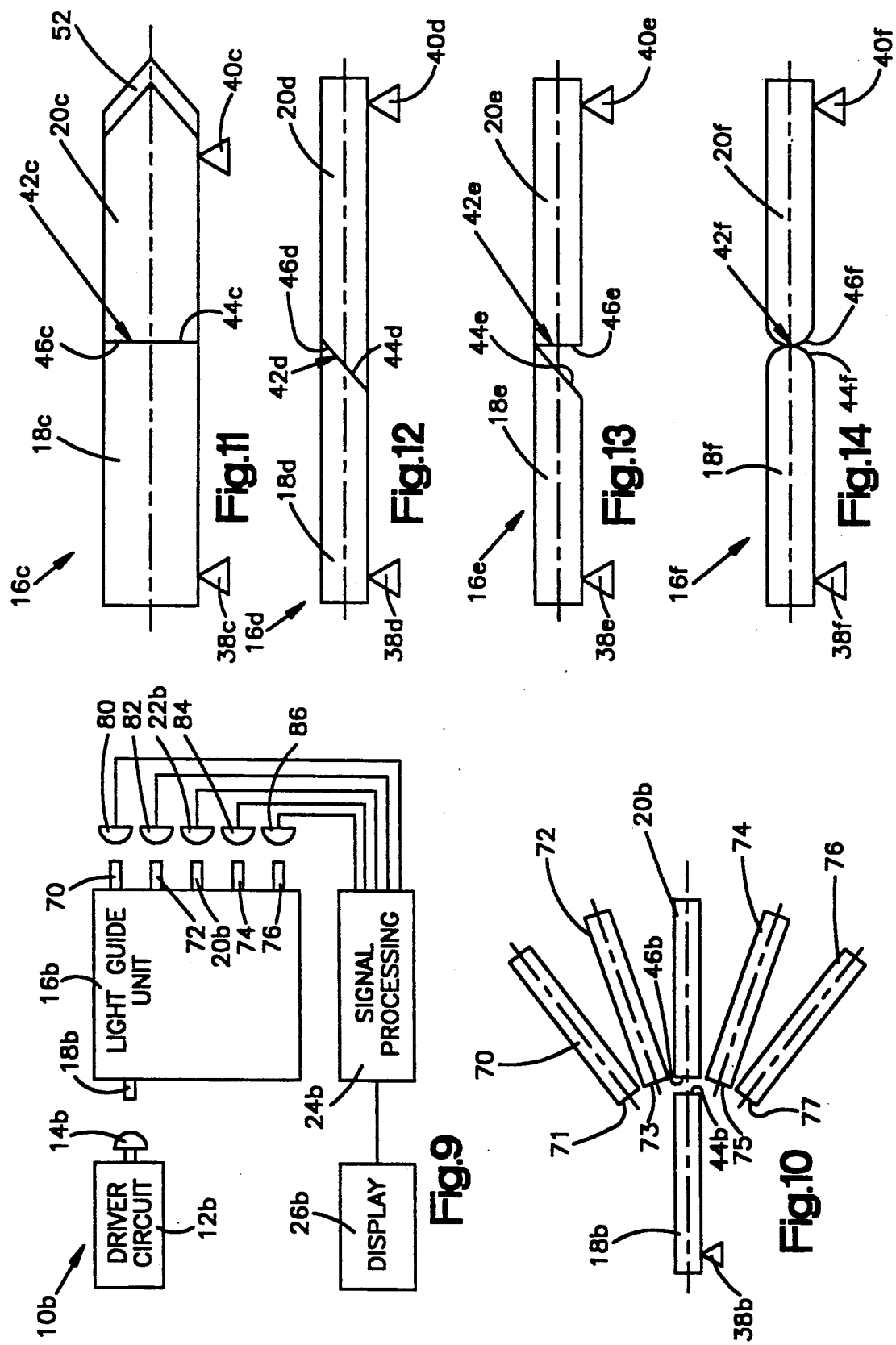

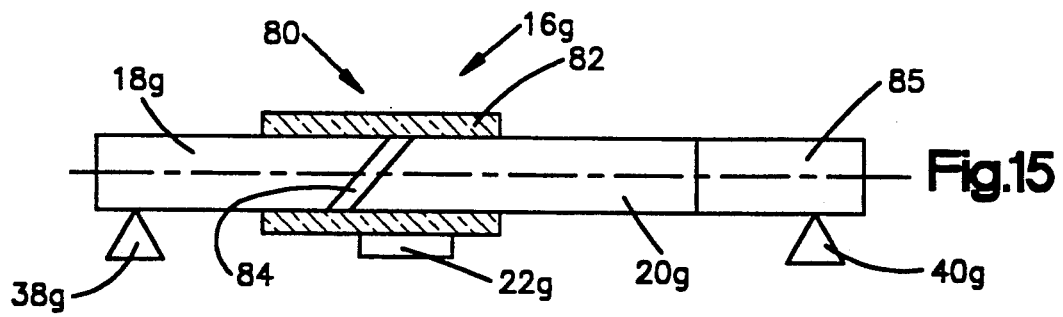
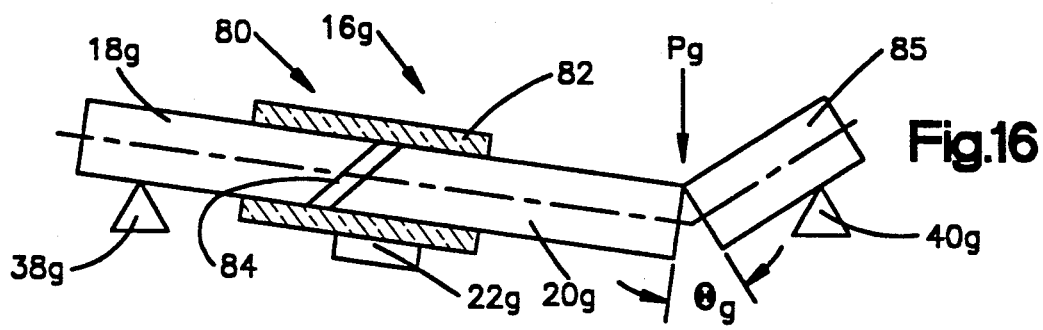
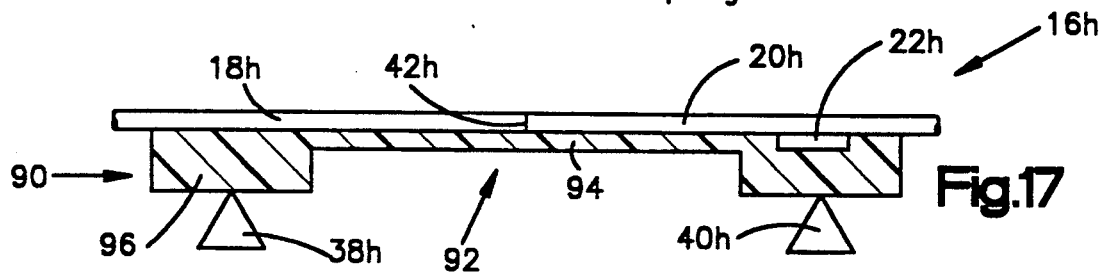
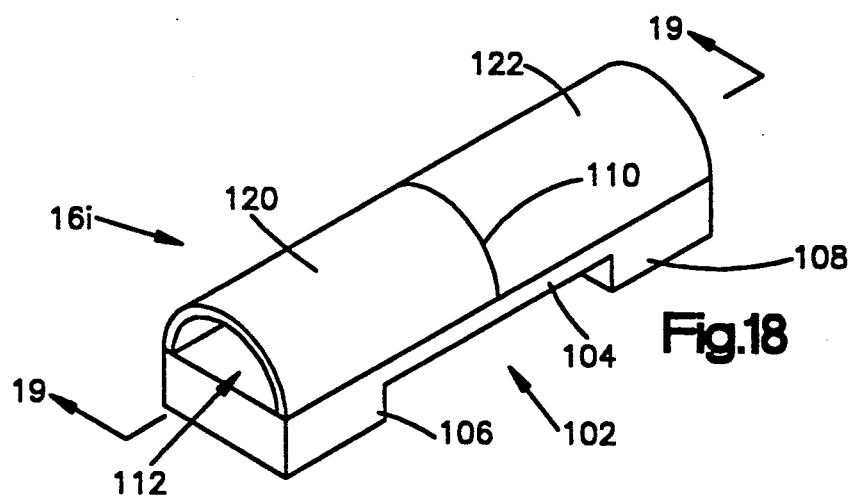
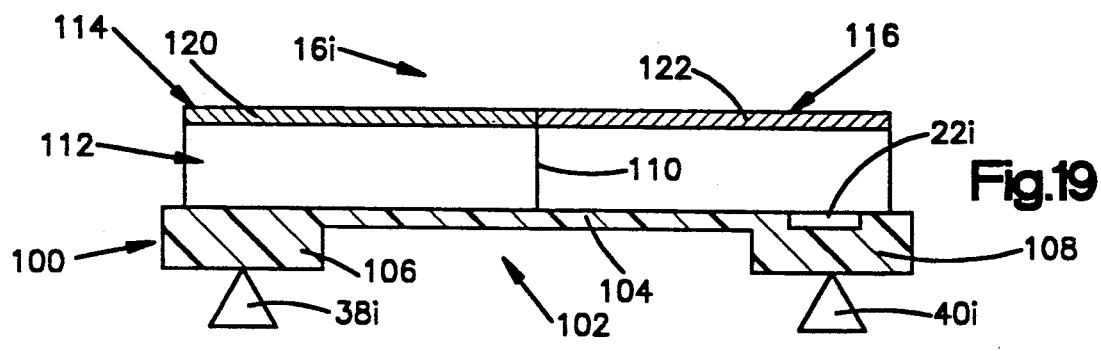

FIBER OPTIC SENSING DEVICE INCLUDING PRESSURE DETECTION AND HUMAN IMPLANTABLE CONSTRUCTION

BACKGROUND OF THE INVENTION

1. Technical Field

The present invention relates to a fiber optic sensing device.

2. Background Art

A multitude of fiber optic sensing devices are known in the art. Such devices are useful in a variety of different applications. A typical use of such devices is in biomedical applications. For example, a fiber optic sensing device may be used as a pressure transducer in a catether for measuring static blood pressure in the human body (in vivo) under variable blood flow conditions. In this type of application, it is desirable to avoid fluid kinetic errors when the blood pressure is being measured.

Fiber optic sensing devices for use in biomedical applications have the advantages of being very small in size, inexpensive, and easy to construct. Also, these fiber optic sensing devices are safe because of their nonelectric nature and are unaffected by electromagnetic interferences. Furthermore, they provide mechanical flexibility and are suitable for long term implantation.

SUMMARY OF THE INVENTION

In accordance with the present invention, a fiber optic sensing device includes a light source and a waveguide for receiving light from the light source and for directing the light in a given direction. Sensing means is provided for sensing light from the waveguide. The device further includes means mounting the waveguide for movement in a direction transverse to the given direction to vary the light transmitted to the sensing means.

In accordance with another aspect of the present invention, a fiber optic sensing device includes a light source and a first fiber optic waveguide for receiving light from the light source. The device further includes a second fiber optic waveguide for receiving light from the first fiber optic waveguide. The device further includes means mounting the first and second fiber optic wave guides for relative movement to vary the light transmitted between the first and second fiber optic waveguides. A sensor is provided for sensing the light transmitted between the first and second fiber optic waveguides.

In one embodiment of the present invention, a fiber optic sensing device is provided for sensing static pressure. The device includes a support and a diaphragm sealably connected in a side wall of the support and which moves in response to changes in static pressure at a location outside of the support. The device further includes a light source and a first fiber optic waveguide on the support for receiving light from the light source. The device further includes a second fiber optic waveguide on the support and which is movable relative to the first fiber optic waveguide for receiving light from the first fiber optic waveguide. The diaphragm acts on at least one of the fiber optic waveguides and effects movement thereof as the diaphragm moves. Thus, the movement between the first and second fiber optic waveguides varies as a function of the static pressure at the location outside of the support. A sensor for sensing light transmitted between the first and second fiber optic waveguides is provided. The light transmitted between the first and second fiber optic waveguides varies as a function of the extent of movement between the first and second fiber optic waveguides. Thus, the light transmitted between the first and second fiber optic waveguides varies as a function of the static pressure at the location outside of the support.

In another embodiment of the present invention, a fiber optic sensing device is provided for sensing angular displacement. The device includes a support, a light source, and a first fiber optic waveguide on the support for receiving light from the light source. The device further includes a second fiber optic waveguide on the support and which is movable relative to the first fiber optic waveguide to form an angle therebetween. The device further includes a sensor for sensing the light transmitted between the first and second fiber optic waveguides. The light transmitted between the first and second fiber optic waveguides varies as a function of the angle formed between the first and second fiber optic waveguides.

BRIEF DESCRIPTION OF THE DRAWINGS

Further features of the present invention will become apparent to those skilled in the art to which the present invention relates from reading the following specification with reference to the accompanying drawings, wherein:

FIG. 1 is a schematic illustration of a pressure measurement system incorporating a fiber optic sensing device constructed in accordance with the present invention;

FIG. 2 is an enlarged, perspective view of a portion of the pressure measurement system of FIG. 1;

FIG. 3 is a longitudinal, cross-sectional view, taken approximately along the line 3—3 of FIG. 2;

FIG. 4 is a partial schematic view of the structure of FIG. 3 showing two fiber optic waveguides aligned in facing relationship to each other;

FIG. 5 is a partial schematic view of the structure of FIG. 4 showing the two fiber optic waveguides in a different position;

FIG. 6 is a sectional view of a second embodiment of the present invention which is a portion of an angular displacement measurement system;

FIG. 7 is a partial schematic view of the structure of FIG. 6 showing two fiber optic waveguides aligned in facing relationship to each other;

FIG. 8 is a partial schematic view of the structure of FIG. 6 showing the two fiber optic waveguides in a different position;

FIG. 9 is a third embodiment of the present invention and schematically illustrates an angular displacement measurement system constructed in accordance with the present invention;

FIG. 10 is a partial schematic view of a portion of the angular displacement measurement system of FIG. 9;

FIG. 11 is a partial schematic view of a fourth embodiment of the present invention;

FIG. 12 is a partial schematic view of a fifth embodiment of the present invention;

FIG. 13 is a partial schematic view of a sixth embodiment of the present invention;

FIG. 14 is a partial schematic view of a seventh embodiment of the present invention;

FIG. 15 is a partial schematic view of an eighth embodiment of the present invention;

FIG. 16 is a partial schematic view of the structure of FIG. 15 showing components in a different position;

FIG. 17 is a sectional view of a ninth embodiment of the present invention showing two fiber optic waveguides disposed on a substrate;

FIG. 18 is a partial perspective view of a tenth embodiment of the present invention; and FIG. 19 is a longitudinal, cross-sectional view, taken approximately along the line 19—19 of FIG. 18.

DESCRIPTION OF PREFERRED EMBODIMENTS

The present invention relates to a fiber optic sensing device. The specific construction and use of the fiber optic sensing device may vary. As an example, the present invention is illustrated in FIG. 1 as embodied in a static pressure measurement system 10. The pressure measurement system 10 includes a driver circuit 12 operatively connected with a light source such as a light emitting diode 14 (LED). The LED 14 emits light in response to signals received from the driver circuit 12. Although the LED 14 is used as the light source, it will be appreciated that any other light source could be used.

The pressure measurement system 10 further includes a light guide unit 16 having a first fiber optic waveguide 18 for receiving light from the LED 14 and a second fiber optic waveguide 20 for receiving light from the first fiber optic waveguide 18. The light transmitted between the first and second fiber optic waveguides 18, 20 varies as a function of pressure applied to the light guide unit 16.

A photodiode 22 is located adjacent to the second fiber optic waveguide 20. The photodiode 22 detects the light from the second fiber optic waveguide 20 and provides an electrical signal indicative thereof. This electrical signal is electrically connected to a signal processing circuit 24. The signal processing circuit 24 processes this electrical signal from the photodiode 22 and generates an output signal which is electrically connected to a display 26. Although the photodiode 22 is used to detect light, it will be appreciated that any other type of light detector could be used.

The output signal of the signal processing circuit 24 varies as a function of the light detected by the photodiode 22. The light in the second fiber optic waveguide 20 received from the first fiber optic waveguide 18 varies as a function of the pressure applied to the light guide unit 16. Thus, the output signal of the signal processing circuit 24 varies as a function of the pressure applied to the light guide unit 16.

The light guide unit 16 is shown in FIG. 2. The components of the light guide unit 16 are preferably constructed of materials suitable for implantation in the human body. The light guide unit 16 includes a support 28 for housing the first and second fiber optic waveguides 18, 20. The tube 28 is of a tubular shape and has a side wall 30 interconnecting two end walls 32, 34 located at opposite axial ends of the tube 28. Although the support 28 has a tubular shape, it is conceivable that the support 28 may be of any shape.

The light guide unit 16 further includes a diaphragm 36 sealably connected in a portion of the side wall 30 of the tube 28. The diaphragm 36 is constructed of a membrane-type of material. The diaphragm 36 deforms (moves) when a pressure is applied thereto. The deformation or mechanical displacement of the diaphragm 36 is functionally related to the pressure applied to the light guide unit 16.

The specific construction of the light guide unit 16 is illustrated in FIG. 3. A block 38 supports the first fiber optic waveguide against the side wall 30 of the tube 28. A block 40 supports the second fiber optic waveguide 20 against the side wall 30 of the tube 28. The first and second fiber optic waveguides 18, 20 are aligned and arranged in abutting relationship at 42.

Referring to FIG. 4, the light guide unit 16 is shown with the fiber optic guides 18, 20 aligned coaxially. In this position, the longitudinal central axis of the first fiber optic waveguide 18 coincides with the longitudinal central axis of the second fiber optic waveguide 20. The first fiber optic waveguide 18 has an end face 44 which is in facing relationship with an end face 46 of the second fiber optic waveguide 20. The end face 44 lies in a plane which extends perpendicular to the longitudinal central axis of the first fiber optic waveguide 18. The end face 46 lies in a plane which extends perpendicular to the longitudinal central axis of the second fiber optic waveguide 20. The first and second fiber optic waveguides 18, 20 are aligned so that the two end faces 44, 46 are in facing relationship to each other, as shown in FIG. 4.

Referring to FIG. 5, when a pressure designated as P is applied to the diaphragm 36 (not shown in FIG. 5), the first and second fiber optic waveguides 18, 20 move relative to each other. For explanation purposes only, the amount of movement of the waveguides 18, 20 is exaggerated. The waveguides 18, 20 are made of a flexible material which enables them to deflect from the position shown in FIG. 4 to a position such as shown in FIG. 5 and to then return toward the position of FIG. 4 when the pressure on the diaphragm is relieved.

The first and second fiber optic waveguides 18, 20 move in a direction which results in an angle, designated as theta, being formed at 42 and between the end face 44 of the first fiber optic waveguide 18 and the end face 46 of the second fiber optic waveguide 20. An angle theta of zero degrees corresponds to the light guide unit 16 being in its unpressured position of FIG. 4. An angle theta of greater than zero degrees corresponds to the light guide unit 16 being in a pressured position. The light received by the second fiber optic waveguide 20 from the first fiber optic waveguide 18 is at a maximum when the angle theta is at zero degrees. The light received is at a maximum because there is no angular misalignment between the first and second fiber optic waveguides 18, 20.

The angle theta increases and the first and second fiber optic waveguides 18, 20 become angularly misaligned when the pressure P is applied to the diaphragm 36. When the angle theta increases and the first and second fiber optic waveguides 18, 20 become misaligned, the light received by the second fiber optic waveguide 20 from the first fiber optic waveguide 18 decreases. This decrease in light received by the second fiber optic waveguide 20 occurs because of light loss caused by angular misalignment between the first and second optic waveguides 18, 20. Thus, as the pressure P applied to the diaphragm 36 increases, the light received by the second fiber optic waveguide 20 from the first fiber optic waveguide 18 decreases because of increased light loss. Likewise, as the pressure P applied to the diaphragm 36 decreases, the angle theta decreases resulting in decreased light loss in the light received by the second fiber optic waveguide 20 from the first fiber optic waveguide 18.

It is contemplated that the fiber optic sensing device of the present invention may be embodied in an angular displacement measurement system. The embodiment of the invention, shown in FIGS. 6-8, is directed to an angular displacement measurement system. Another embodiment of the invention, shown in FIGS. 9-10, is also directed to an angular displacement measurement system.

Referring to FIG. 6, a second embodiment of the present invention is shown. Since the embodiment of the invention shown in FIG. 6 is generally similar to the embodiment of the invention shown in FIGS. 1-5, similar numerals will be utilized to designate similar components, the suffix letter "a" being associated with the components of FIG. 6 to avoid confusion.

The light guide unit 16a includes a tubular shaped support 28a in which first and second fiber optic waveguides 18a, 20a are disposed. The first and second fiber optic waveguides 18a, 20a are supported against the support 28a with blocks 38a, 40a.

A portion of the outside of the support 28a is secured to a fixed reference frame 62. As shown in FIG. 6, one end of the tubular support 28a near the block 40a is secured to the fixed reference frame 62. A connecting block 60 is secured between the fixed reference frame 62 and a central portion of the outside of the tubular support 28a. As shown in FIG. 6, the connecting block 60 is connected to the outside of the support 28a and slightly to the right of 42a between the first and second fiber optic waveguides 18a, 20a.

Referring to FIG. 7, the light guide unit 16a is shown in one position. In this position, the longitudinal central axis of the first fiber optic waveguide 18a coincides with the longitudinal central axis of the second fiber optic waveguide 20a. The first and second fiber optic waveguides 18a, 20a are aligned so that the two end faces 44a, 46a are in facing relationship to each other as shown in FIG. 7.

Referring to FIG. 8, when a force designated as F is applied to a point near the block 38a, the first fiber optic waveguide 18a moves relative to the second fiber optic waveguide 20a. The support 28a (not shown in FIG. 8) is made of a flexible material which enables the waveguides 18a, 20a to deflect from the position shown in FIG. 7 to a position such as shown in FIG. 8 and to then return toward the position of FIG. 7 when the force applied to the point near the block 38a is relieved. The flexible material gives the support 28a its bending and resiliency characteristics. The movement of the first fiber optic waveguide 18a is such that the first fiber optic waveguide 18a pivots about an axis substantially near the connecting block 60. The first fiber optic waveguide 18a pivots because the second fiber optic waveguide 20a is held secured relative to the fixed reference frame 62.

When the first fiber optic waveguide 18a pivots about the axis near the connecting block 60, an angle, designated as theta (a), is formed at 42a and between the end faces 44a, 46a. An angle theta (a) of zero degrees corresponds to the light guide unit 16a being in its unpressured position of FIG. 7. An angle greater than zero degrees corresponds to the light guide unit 16a being in a pressured position of FIG. 8. The light received by the second fiber optic waveguide 20a from the first fiber optic waveguide 20a is in the same manner as that described in the first embodiment shown in FIGS. 1-5.

Referring to FIGS. 9-10, a third embodiment of the present invention is shown. Since the embodiment of the invention shown in FIGS. 9-10 is generally similar to the embodiment of the invention shown in FIGS. 1-5, similar numerals will be utilized to designate similar components, the suffix letter "b" being associated with the components of FIGS. 9-10 to avoid confusion.

An angular displacement measurement system 10b includes a light guide unit 16b. The light guide unit 16b includes a first optic waveguide 18b and five other fiber optic waveguides 20b, 70, 72, 74 and 76. Each of the five fiber optic waveguides 20b, 70, 72, 74 and 76 has an associated photodiode. These photodiodes are designated as 22b, 80, 82, 84 and 86, respectively, for each of the five fiber optic waveguides 20b, 70, 72, 74 and 76. Each of the five fiber optic waveguides 20b, 70, 72, 74 and 76 are arranged in a spatial relationship relative to each other and relative to the first fiber optic waveguide 18b in a manner as shown in FIG. 10. The five fiber optic waveguides 20b, 70, 72, 74 and 76 have end faces 46b, 71, 73, 75, and 77, respectively. The end faces 46b, 71, 73, 75 and 77 are in a predetermined facing relationship with an end face 44b of the first fiber optic waveguide 18b.

As shown in FIG. 10, the light guide unit 16b is shown in one position. In this position, the longitudinal central axis of the first fiber optic waveguide 18b coincides with the longitudinal central axis of the fiber optic waveguide 20b. The light received by the fiber optic waveguide 20b from the first fiber optic waveguide 18b is at a maximum when the light guide unit 16b is in the position of FIG. 10. When the first fiber optic waveguide 18b moves relative to the five fiber optic waveguides 20b, 70, 72, 74 and 76, the light transmitted from the first fiber optic waveguide 18b to each of the five fiber optic waveguides 20b, 70, 72, 74 and 76 varies as a function of the direction and extent of movement of the first fiber optic waveguide 18b. The first fiber optic waveguide 18b is pivotally mounted to a block 38b in a manner which allows the first fiber optic waveguide 18b to move between a position in which the end face 44b is in facing relationship with the end face 71 of the fiber optic waveguide 70 to a position in which the end face 44b is in facing relationship with the end face 77 of the fiber optic waveguide 76. Thus, the direction and extent of movement of the first fiber optic waveguide 18b about the pivot point near the block 38b can be sensed and measured.

The embodiment of the invention shown in FIG. 11 is generally similar to the embodiment of the invention shown in FIGS. 1-5. Similar numerals will be utilized to designate similar components, the suffix letter "c" being associated with the components of FIG. 11 to avoid confusion.

The light guide unit 16c includes a first fiber optic waveguide 18c and a mirror assembly 52 connected within one end of a second fiber optic waveguide 20c. The first and second fiber optic waveguides 18c, 20c are aligned so that their longitudinal central axes coincide when the light guide unit 16c is in the position of FIG. 11. Light received by the second fiber optic waveguide 20c from the first fiber optic waveguide 18c is reflected off of the mirror assembly 52 back to the first fiber optic waveguide 18c. This reflected light is eventually detected by a photodiode 22c (not shown in FIG. 11). The light directed to the mirror assembly 52 and the light reflected therefrom is at a maximum when the first and second fiber optic waveguides 18c, 20c are aligned so that their longitudinal central axes coincide.

When the first and second fiber optic waveguides 18c, 20c become misaligned, the light transmitted to the mirror assembly 52 and the light reflected therefrom decreases. This has the effect of providing greater sensitivity in the device incorporating the use of the light guide unit 16c. The sensitivity is greater because there is light loss when the second fiber optic waveguide 20c receives light from the first fiber optic waveguide 18c and also when the first fiber optic waveguide 18c receives the reflected light from the second fiber optic waveguide 20c.

The embodiment of the invention shown in FIG. 12 is generally similar to the embodiment of the invention shown in FIGS. 1-5. Similar numerals will be utilized to designate similar components, the suffix letter "d" being associated with the components of FIG. 12 to avoid confusion.

The light guide unit 16d includes a first fiber optic waveguide 18d having an end face 44d. The end face 44d lies in a plane which extends in a direction not perpendicular to the longitudinal central axis of the first fiber optic waveguide 18d. The second fiber optic waveguide 20d has an end face 46d. The end face 46d lies in a plane which extends in a direction not perpendicular to the longitudinal central axis of the second fiber optic waveguide 20d. The two end faces 44d, 46d of the first and second fiber optic waveguides 18d, 20d are in facing relationship to each other as shown in FIG. 12. The light received by the second fiber optic waveguide 20d from the first fiber optic waveguide 18d is in the same manner as that described in the first embodiment shown in FIGS. 1-5.

The embodiment of the invention shown in FIG. 13 is generally similar to the embodiment of the invention shown in FIGS. 1-5. Similar numerals will be utilized to designate similar components, the suffix letter "e" being associated with the components of FIG. 13 to avoid confusion.

The light guide unit 16e includes a first fiber optic waveguide 18e having an end face 44e. The end face 44e lies in a plane which extends in a direction not perpendicular to the longitudinal central axis of the first fiber optic waveguide 18e. The second fiber optic waveguide 20e includes an end face 42e. The end face 46e lies in a plane which extends in a direction perpendicular to the longitudinal central axis of the second fiber optic waveguide 20e. The end face 44e is in facing relationship with the end face 46e as shown in FIG. 13. The light received by the second fiber optic waveguide 20e from the first fiber optic waveguide 18e is in the same manner as that described in the first embodiment shown in FIGS. 1-5.

The embodiment of the invention shown in FIG. 14 is generally similar to the embodiment of the invention shown in FIGS. 1-5. Similar numerals will be utilized to designate similar components, the suffix letter "f" being associated with the components of FIG. 14 to avoid confusion.

A first fiber optic waveguide 18f has a rounded end face 44f. A second fiber optic waveguide 20f has a rounded end face 46f. The rounded end faces 44f, 46f are in facing relationship with respect to each other as shown in FIG. 14. Although both end faces 44f, 46f are rounded in shape, it is conceivable that only one of the end faces may be rounded in shape and the other one of the end faces may lie in a plane which extends perpendicular to the longitudinal central axis of its associated fiber optic waveguide. The light received by the second fiber optic waveguide 20f from the first fiber optic waveguide 18f is in the same manner as that described in the first embodiment shown in FIGS. 1-5.

The embodiment of the invention shown in FIGS. 15-16 is generally similar to the embodiment of the invention shown in FIGS. 1-5. Similar numerals will be utilized to designate similar components, the suffix letter "g" being associated with the components of FIGS. 15-16 to avoid confusion.

The light guide unit 16g includes a first fiber optic waveguide 18g for receiving light from a light source (not shown in FIGS. 15-16) at one end of the first fiber optic waveguide 18g. The other end of the first fiber optic waveguide 18g is fixedly secured within one end of a cylindrical-shaped optical assembly 80. One end of a second fiber optic waveguide 20g is fixedly secured within the other end of the optical assembly 80.

The optical assembly 80 includes a transparent, cylindrical-shaped housing 82 having an optical element 84 disposed within the housing 82. Although the housing 82 is shown as cylindrical, it is possible that the housing 82 could be of any other shape, such as either rectangular or square. The optical element 84 is flat in shape and lies in a plane which extends at an acute angle to the longitudinal central axis of the optical assembly 80. The optical characteristics of the optical element 84 are such that (1) light transmitted from the first fiber optic waveguide 18g toward the second fiber optic waveguide 20g is passed through the optical element 84, and (2) light transmitted from the second fiber optic waveguide 20g toward the first optic waveguide 18g is reflected by the optical element 84 downward as viewed in FIG. 15 and through the transparent housing 82.

A light sensor 22g is mounted on a side wall of the housing 82. The sensor 22g is mounted in a position which allows it to sense any light reflected off of the optical element 84 of the optical assembly 80. A mirror assembly 85 is pivotally mounted at the other end of the second fiber optic waveguide 20g. The light guide unit 16g further includes a housing (not shown in FIGS. 15-16) made of a flexible material for supporting the structure of FIGS. 15-16. This flexible material is like the flexible material of the support 28a discussed with respect to the embodiment of FIGS. 6-8.

As shown in FIG. 16, when a pressure designated as $P_g$ is applied to the light guide unit 16g, the second fiber optic waveguide 20g and the mirror assembly 85 move with respect to each other to form an angle theta (g) therebetween. For explanation purposes only, the amount of movement between the second fiber optic waveguide 20g and the mirror assembly 85 is exaggerated. When this movement occurs, the light directed to the mirror assembly 85 and reflected from the mirror assembly 85 toward the optical element 84 changes. The light reflected from the mirror assembly 85 to the optical element 84 is at a maximum when the angle theta (g) is at zero degrees. As the angle theta (g) increases, the light sensed by the sensor 22g decreases because of increased light loss in the light reflected from the mirror assembly 85 to the optical element 84. Thus, as the angle theta (g) increases, the light received by the sensor 22g from the optical element 84 decreases.

Although a mirror assembly is shown in FIGS. 15-16, it is contemplated that it may be preferred to connect a photosensor to the one end of the second fiber optic waveguide 20g in place of the mirror assembly 85. In this arrangement, the angle theta (g) increases as the pressure $P_g$ applied to the light guide unit 16g increases. Thus, the light received by the photodiode from the optical element 84 would decrease as the pressure $P_g$ is applied to the light guide unit 16g increases.

The embodiment of the invention shown in FIG. 17 is generally similar to the embodiment of the invention shown in FIGS. 1-5. Similar numerals will be utilized to designate similar components, the suffix letter "h" being associated with the components of FIG. 17 to avoid confusion.

A light guide unit 16h includes a first fiber optic waveguide 18h having an end face 44h. The end face 44h lies in a plane which extends in a direction perpendicular to the longitudinal central axis of the first fiber optic waveguide 18h. A second fiber optic waveguide 20h has an end face 46h. The end face 46h lies in a plane which extends in a direction perpendicular to the longitudinal central axis of the second fiber optic waveguide 20h. The two end faces 44h, 46h of the first and second fiber optic waveguides 18h, 20h are in facing relationship to each other, as shown in FIG. 17. In the position as shown in FIG. 17, the longitudinal central axis of the first fiber optic waveguide 18h coincides with the longitudinal central axis of the second fiber optic waveguide 20h.

The first and second fiber optic waveguides 18h, 20h lie on a substrate 90, such as a silicon wafer. The substrate 90 has an etched out portion 92 located at the central portion of the substrate 90. This etched portion 92 is formed using etching techniques as known in the art, and therefore, will not be discussed.

By forming the etched portion 92, a thin substrate portion 94 interconnects two thick substrate portions 96, 98. The thin substrate portion 94 has bending characteristics which enable the first and second fiber optic waveguides 18h, 20h to move with respect to each other when pressure is applied to the light guide unit 16h. Furthermore, the thin substrate portion 94 has resiliency characteristics which enable the first and second fiber optic waveguides 18h, 20h to return to the position shown in FIG. 17 when pressure applied to the light guide unit 16h is relieved.

A light sensor 22h is disposed in the substrate 90 at one end thereof. A housing (not shown in FIG. 17) supports the structure shown in FIG. 17. The housing is made of a flexible material like that of the support 28a in the embodiment of FIGS. 6-8. The light received by the second fiber optic waveguide 20h from the first fiber optic waveguide 18h is in the same manner as that described in the first embodiment shown in FIGS. 1-5. The light sensed by the light sensor 22h varies as a function of the light transmitted from the first fiber optic waveguide 18h to the second fiber optic waveguide 20h. When pressure is applied to the light guide unit 16h at 42h, the first and second fiber optic waveguides 18h, 20h move in the same manner as described with respect to FIGS. 1-5.

The embodiment of the invention shown in FIGS. 18-19 is generally similar to the embodiment of the invention shown in FIGS. 1-5. Similar numerals will be utilized to designate similar components, the suffix letter "i" being associated with the components of FIGS. 18-19 to avoid confusion.

The light guide unit 16i includes a substrate 100, such as a silicon wafer. The substrate 100 has an etched portion 102 located at the central portion of the substrate 100. This etched portion 102 is formed using etching techniques as known in the art, and therefore, will not be discussed. By forming the etched portion 102, a thin substrate portion 104 interconnects two thick substrate portions 106, 108. The light guide unit 16i further includes a first wall-forming layer 120 disposed on the substrate 100 and a second wall-forming layer 122 disposed on the substrate 100. The first and second wall-forming layers 120, 122 are aligned and in abutting relationship at 110. Each of the wall-forming layers 120, 122 is of a semi-cylindrical shape as shown in FIG. 18. However, it is conceivable that the wall-forming layers 120, 122 may be of any shape such as a rectangular shape or a square shape.

The substrate 100 and the two wall-forming layers 120, 122 are arranged to form a channel 112 therebetween. The channel 112 is fabricated using known techniques disclosed in U.S. application Ser. No. 936,887, and therefore, will not be discussed. The channel 112 acts to direct light transmitted therethrough A light sensor 22i is located at one end of the channel 112 and is disposed in at least a portion of the substrate 100. The light guide unit 16i further includes a housing (not shown in FIGS. 18-19) made of a flexible material for supporting the structure of FIGS. 18-19. This flexible material is like the flexible material of the support 28a discussed with respect to the embodiment of FIGS. 6-8.

The structure of a portion of the substrate 100 and the first wall-forming layer 120 functions as a first light waveguide 114. The structure of a portion of the substrate 100 and the second wall-forming layer 122 functions as a second light waveguide 116. The thin substrate portion 104 has bending characteristics which enable the first and second light waveguides 114, 116 to move with respect to each other when pressure is applied to the light guide unit 16i. Furthermore, the thin substrate portion 104 has resiliency characteristics which enable the first and second light waveguides 114, 116 to return to the position shown in FIG. 19 when pressure applied to the light guide unit 16i is relieved.

The first light waveguide 114 receives light from a light source (not shown in FIGS. 18-19). This light is transmitted to the second light waveguide 116 and is sensed by the light sensor 22i. The light received by the second light waveguide 116 from the first light waveguide 114 is in a manner similar to that of the fiber optic waveguides described in the first embodiment shown in FIGS. 1-5. The light sensed by the light sensor 22i varies as a function of the light transmitted from the first light waveguide 114 to the second light waveguide 116. When pressure is applied to the light guide unit 16i at 110, the first and second light waveguides 114, 116 move in a manner similar to that of the fiber optic waveguides described with respect to the first embodiment shown in FIGS. 1-5.

It is contemplated that the embodiments of the present invention shown in FIGS. 11-19 may be embodied in the pressure measurement system described in FIGS. 1-5. It is also contemplated that the embodiments of the present invention shown in FIGS. 11-19 may be embodied in the angular displacement measurement systems described in FIGS. 6-10.

This invention has been described above with reference to preferred embodiments. Modifications and alterations may become apparent to one skilled in the art upon reading and understanding the specification. It is intended to include all such modifications and alterations within the scope of the appended claims.

Having described preferred embodiments of the invention, I claim:

1. A fiber optic sensing device comprising:
a light source;
a first fiber optic waveguide for receiving light from said light source;
a second fiber optic waveguide for receiving light from said first fiber optic waveguide;
mounting means for mounting said first and second fiber optic waveguides in an unexcited state and for allowing relative movement between said first waveguide and said second waveguide in response to a stimuli to vary the light transmitted between said first and second fiber optic wave guides; and
sensing means for sensing the light transmitted between said first and second fiber optic waveguides;
wherein the light transmitted between said first and second fiber optic waveguides is a maximum at said unexcited state;
wherein said first and second fiber optic waveguides are constructed in a manner suitable for implantation in the human body.

2. The fiber optic sensing device of claim 1 wherein said light source is a light-embitting diode and wherein said sensor sensing the light transmitted between said first and second fiber optic waveguides includes a photodiode.

3. The fiber optic sensing device of claim 1 wherein said mounting means includes a photodiode connected at one end of one of said waveguides, said photodiode sensing light received by said one waveguide from said light source.

4. The fiber optic device of claim 1 wherein said first waveguide has a longitudinal central axis and an end face; wherein said second waveguide has a longitudinal central axis and an end face positioned adjacent to said end face of said first waveguide; and wherein said end faces of said waveguides are arranged and aligned in abutting relationship in said unexcited state.

5. A fiber optic sensing device comprising:
a light source;
a first fiber optic waveguide for receiving light from said light source;
a second fiber optic waveguide for receiving light from said first fiber optic waveguide;
mounting means for mounting said first and second fiber optic waveguides in an unexcited state and for allowing relative movement between said first waveguide and said second waveguide in response to a stimuli to vary the light transmitted between said first and second fiber optic wave guides; and
sensing means for sensing the light transmitted between said first and second fiber optic waveguides;
wherein the light transmitted between said first and second fiber optic waveguides is a maximum at said unexcited state; and
wherein said means mounting said first and second fiber optic waveguides includes a tubular-shaped housing in which said first and second fiber optic waveguides are disposed.

6. A fiber optic sensing device for sensing static pressure comprising:
a housing;
a diaphragm means sealably connected in a side wall of said housing for sensing static pressure at a location outside of said housing;
a light source;
a first fiber optic waveguide in said housing for receiving light from said light source;
a second fiber optic waveguide mounted in said housing in an unexcited state and movable relative to said first fiber optic waveguide for receiving light from said first fiber optic waveguide, the movement between said first and second fiber optic waveguides varying as a function of the movement of the diaphragm means responsive to changes in static pressure at the location outside said housing; and
a sensor sensing light transmitted between said first and second fiber optic waveguides, the light transmitted between said first and second fiber optic waveguides being at a maximum at said unexcited state and varying as a function of the extent of movement between said first and second fiber optic waveguides, and thereby varying as a function of the static pressure at the location outside of said housing;
wherein said first and second fiber optic waveguides are constructed in a manner suitable for implantation in the human body.

7. The fiber optic sensing device of claim 6 wherein said diaphragm means includes a membrane in which mechanical deformation is functionally related to a pressure applied thereto.

8. The fiber optic sensing device of claim 6 wherein said light source is a light-emitting diode and wherein said sensor for sensing light transmitted between said first and second fiber optic waveguides includes a photodiode.

9. A fiber optic sensing device comprising:
a light source;
a first fiber optic waveguide for receiving light from said light source;
a second fiber optic waveguide for receiving light from said first fiber optic waveguide;
mounting means for mounting said first and second fiber optic waveguides in an unexcited state and for allowing relative movement between said first waveguide and said second waveguide in response to a stimuli to vary the light transmitted between said first and second fiber optic wave guides; and
sensing means for sensing the light transmitted between said first and second fiber optic waveguides;
wherein the light transmitted between said first and second fiber optic waveguides is a maximum at said unexcited state; and
wherein said mounting means includes a mirror assembly pivotally connected at one end of said second waveguide.

10. The fiber optic sensing device of claim 9 wherein said sensing means is connected with one of said waveguides and senses light reflected from said mirror assembly.

11. A fiber optic sensing device comprising:
a light source;
a first fiber optic waveguide for receiving light from said light source;
a second fiber optic waveguide for receiving light from said first fiber optic waveguide;
mounting means for mounting said first and second fiber optic waveguides in an unexcited state and for allowing relative movement between said first waveguide and said second waveguide in response to a stimuli to vary the light transmitted between said first and second fiber optic wave guides; and
sensing means for sensing the light transmitted between said first and second fiber optic waveguides;

wherein the light transmitted between said first and second fiber optic waveguides is a maximum at said unexcited state;
wherein mounting means includes a substrate on which said first and second waveguides are mounted;
wherein said mounting means further includes a housing enclosing the waveguides and the substrate.

12. The fiber optic sensing device of claim 11 wherein said sensing means is disposed in at least a portion of said substrate.

13. A fiber optic sensing device comprising:
a light source;
a first fiber optic waveguide for receiving light from said light source;
a second fiber optic waveguide for receiving light from said first fiber optic waveguide;
mounting means for mounting said first and second fiber optic waveguides in an unexcited state and for allowing relative movement between said first waveguide and said second waveguide in response to a stimuli to vary the light transmitted between said first and second fiber optic wave guides; and
sensing means for sensing the light transmitted between said first and second fiber optic waveguides;
wherein the light transmitted between said first and second fiber optic waveguides is a maximum at said unexcited state;
wherein said mounting means includes a substrate on which said first and second waveguides are mounted; and
wherein said substrate is a silicon wafer.

14. A fiber optic sensing device comprising:
a light source;
a first fiber optic waveguide for receiving light from said light source;
a second fiber optic waveguide for receiving light from said first fiber optic waveguide;
mounting means for mounting said first and second fiber optic waveguides in an unexcited state and for allowing relative movement between said first waveguide and said second waveguide in response to a stimuli to vary the light transmitted between said first and second fiber optic wave guides; and
sensing means for sensing the light transmitted between said first and second fiber optic waveguides;
wherein the light transmitted between said first and second fiber optic waveguides is a maximum at said unexcited state;
wherein said mounting means includes a substrate on which said first and second waveguides are mounted; and
wherein said waveguide includes a wall forming layer disposed in said substrate, said wall forming layer and said substrate forming a channel therebetween for directing light received from said light source.

15. The fiber optic sensing device of claim 14 wherein said sensing means is disposed in at least a portion of said substrate.

16. The fiber optic sensing device of claim 14 wherein said mounting means further includes a housing enclosing the waveguides and the substrate.

17. A fiber optic sensing device comprising:
a light source;
a first fiber optic waveguide for receiving light from said light source;
a second fiber optic waveguide for receiving light from said first fiber optic waveguide;
mounting means for mounting said first and second fiber optic waveguides in an unexcited state and for allowing relative movement between said first waveguide and said second waveguide in response to a stimuli to vary the light transmitted between said first and second fiber optic wave guides; and
sensing means for sensing the light transmitted between said first and second fiber optic waveguides;
wherein the light transmitted between said first and second fiber optic waveguides is a maximum at said unexcited state;
wherein said first waveguide has a longitudinal central axis and an end face;
wherein said second waveguide has a longitudinal central axis and an end face positioned adjacent to said end face of said first waveguide;
wherein said end faces of said waveguides are arranged and aligned in abutting relationship in said unexcited state; and
wherein the end face of one of said waveguides extends in a direction unperpendicular to the longitudinal axis of said waveguide.

18. The fiber optic device of claim 17 wherein the end face of the other of said waveguides extends in a direction unperpendicular to the longitudinal axis of said waveguide.

19. The fiber optic device of claim 17 wherein the end face of the other of said waveguides extends in a direction perpendicular to the longitudinal axis of said waveguide.

20. A fiber optic sensing device comprising:
a light source;
a first fiber optic waveguide for receiving light from said light source;
a second fiber optic waveguide for receiving light from said first fiber optic waveguide;
mounting means for mounting said first and second fiber optic waveguides in an unexcited state and for allowing relative movement between said first waveguide and said second waveguide in response to a stimuli to vary the light transmitted between said first and second fiber optic wave guides; and
sensing means for sensing the light transmitted between said first and second fiber optic waveguides;
wherein the light transmitted between said first and second fiber optic waveguides is a maximum at said unexcited state;
wherein said first waveguide has a longitudinal central axis and an end face;
wherein said second waveguide has a longitudinal central axis and an end face positioned adjacent to said end face of said first waveguide;
wherein said end faces of said waveguides are arranged and aligned in abutting relationship in said unexcited state; and
wherein the end face of one of said waveguides is rounded.

21. The fiber optic device of claim 20 wherein the end face of the other of said waveguides is rounded.

22. A fiber optic sensing device for sensing static pressure comprising:
a housing;
diaphragm means sealably connected in a side wall of said housing for sensing static pressure at a location outside of said housing;
a light source;

a first fiber optic waveguide in said housing for receiving light from said light source;

a second fiber optic waveguide mounted in said housing in an unexcited state and movable relative to said first fiber optic waveguide for receiving light from said first fiber optic waveguide, the movement between said first and second fiber optic waveguides varying as a function of the movement of the diaphragm means responsive to changes in static pressure at the location outside said housing; and a sensor sensing light transmitted between said first and second fiber optic waveguides, the light transmitted between said first and second fiber optic waveguides being at a maximum at said unexcited state and varying as a function of the extent of movement between said first and second fiber optic waveguides, and thereby varying as a function of the static pressure at the location outside of said housing;

wherein said housing is of a tubular shape in which said first and second fiber optic waveguides are disposed.

* * * * *